United States Patent
Takechi et al.

(10) Patent No.: US 6,248,920 B1
(45) Date of Patent: *Jun. 19, 2001

(54) PREPARATION PROCESS FOR ESTERS AND RESIST MATERIALS

(75) Inventors: Satoshi Takechi, Kawasaki; Tadashi Kikukawa, Kyoto, both of (JP)

(73) Assignee: Fujitsu Limited, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/996,158

(22) Filed: Dec. 22, 1997

(30) Foreign Application Priority Data

Dec. 27, 1996 (JP) .................................................. 8-350765

(51) Int. Cl.$^7$ .................................................. C07C 69/74
(52) U.S. Cl. ......................... 560/116; 560/117; 560/210; 560/238
(58) Field of Search ..................... 560/116, 117, 560/210, 238

(56) References Cited

U.S. PATENT DOCUMENTS

| | | | |
|---|---|---|---|
| 3,686,286 | * 8/1972 | Ahn et al. | 560/236 |
| 3,843,719 | * 10/1974 | Brady | 558/415 |
| 4,068,082 | * 1/1978 | Stoffey et al. | 560/90 |
| 4,153,568 | * 5/1979 | Light et al. | 510/105 |
| 4,518,796 | * 5/1985 | Aoshima et al. | 560/208 |
| 4,581,471 | * 4/1986 | Barlow et al. | 560/210 |
| 5,459,067 | * 10/1995 | Kageyama et al. | 435/280 |

FOREIGN PATENT DOCUMENTS 4-39665   2/1992   (JP) .

OTHER PUBLICATIONS

Michael B. Smith, Asymmetric Induction, Organic Synthesis, p. 706–707, Mar. 1996.*

* cited by examiner

Primary Examiner—Gary Geist
Assistant Examiner—Taylor V. Oh
(74) Attorney, Agent, or Firm—Armstrong, Westerman, Hattori, McLeland & Naughton, LLP

(57) ABSTRACT

Process for the quantitative preparation of esters, with a high yield, which comprises reacting an aldehyde or ketone compound and an acid halide compound in a one pot reaction in the presence of at least one compound represented by the following formulae:

RMgX                    (I);

RMgX/CuX                (II); and

RLi or R(CuLi)$_{1/2}$   (III);

in which R represents a hydrocarbon group, and X represents a halogen atom. Production processes of a resist material and a semiconductor device are also disclosed.

10 Claims, No Drawings

PREPARATION PROCESS FOR ESTERS AND RESIST MATERIALS

BACKGROUND OF THE INVENTION

1. Field of the Invention

The present invention relates to a process for the preparation of esters, more particularly, a process for the preparation of esters having a large steric hindrance. According to the present invention, the target esters can be easily and effectively prepared. The present invention also relates to a process for the preparation of a chemically amplified resist material comprising an alicyclic hydrocarbon group-containing polymer, which comprises polymerizing esters after they were prepared in accordance with the preparation process of the present invention. As will be appreciated from the descriptions of this specification, the term "polymer" used herein is intended to mean both a homopolymer and a copolymer which is produced by the simultaneous polymerization of two, three or more dissimilar monomeric compounds or monomers. The chemically amplified resist material can exhibit a high resolution, a high sensitivity and an excellent resistance to dry etching. The resist composition of the present invention can exhibit a high sensitivity and stable patterning properties which are particularly desired in the field of KrF and ArF lithography. In addition, the present invention relates to a process for the production of a semi-conductor devices such as semiconductor integrated circuits, for example, LSIs, VLSIs, ULSIs and other devices, using the chemically amplified resist material of the present invention in a lithographic process.

2. Description of the Related Art

Recently, in the field of the production of semiconductor devices, to satisfy the requirements for the formation of fine resist patterns, attention has been made to a chemically amplified resist material and lithographic process using such material. At present, a wide variety of chemically amplified resist materials are well known.

For example, as is disclosed in Japanese Unexamined Patent Publication (Kokai) No. 4-39665, the inventor of the present application has invented a chemically amplified resist material characterized by comprising a polymer or copolymer of acrylic acid ester or a-substituted acrylic acid ester in which the ester portion contains an adamantane skeleton. The chemically amplified resist material can be effectively used in the formation of submicron-ordered resist patterns using as a patterning radiation the radiation in the range of far ultraviolet or vacuum ultraviolet lights, because they have an excellent transparency to the patterning radiation and also a high resistance to dry etching.

The resist polymers or copolymers containing the above-described ester structure are generally produced by reacting an alcohol containing the part corresponding to said ester structure with an acid or acid halide, that is, using conventional esterification methods, to produce an ester, followed by conducting a polymerization reaction using the ester as a starting monomer. However, the production process has a drawback in that, using the conventional methods, it is difficult to easily, effectively and stably carry out the preparation of the ester. For example, the previous preparation of an alcohol as the starting material is troublesome. Further, if the esterification of a tertiary alcohol is carried out to obtain a target ester, a dissociation reaction may be caused in the resulting ester due to the presence of stable carbocations, and an esterification reaction itself is inhibited due to the steric hindrance of the contained substituents.

SUMMARY OF THE INVENTION

Accordingly, one object of the present invention is to provide a process for the easy and stable preparation of esters, having large steric hindrance, with a high yield.

Another object of the present invention is to provide a process for the easy preparation of a resist material having excellent performances by using the simplified steps.

Still another object of the present invention is to provide a process for the production of a semiconductor device using the above-described resist material of the present invention.

Other objects of the present invention will be appreciated from the below-mentioned detailed description of the present invention.

In one aspect thereof, the present invention provides a process, for the preparation of esters, which comprises reacting an aldehyde or ketone compound and an acid halide compound in a one pot reaction in the presence of at least one compound represented by the following formulae (I), (II) and (III):

$$RMgX \hspace{2cm} (I);$$

$$RMgX/CuX \hspace{2cm} (II); \text{ and}$$

$$RLi \text{ or } R(CuLi)_{1/2} \hspace{2cm} (III);$$

in which
  R represents a hydrocarbon group, and
  X represents a halogen atom.

According to the preparation process of the present invention, since the aldehyde or ketone compound and the acid halide compound are used as the starting material for the esterification reaction, and also the esterification reaction is carried out in the presence of the specific Gringnard compound and/or an organic lithium compound, the esterification reaction can proceed quantitatively, thus ensuring a high yield as a result of easy purification of the products. Further, since there is no necessity to previously synthesize the corresponding alcohol as in the conventional methods, the reaction steps can be included in a so-called "one pot reaction", thereby ensuring a simplified production process. Further, in addition to the simplification of the production process, it becomes possible to prepare a wide variety of ester compounds by suitably selecting the aldehyde or ketone compound and the Gringnard compound and/or the organic lithium compound. In particular, it has been found that the preparation process of the present invention can be very effectively carried out if the aldehyde or ketone compound used contains an alicyclic hydrocarbon group such as adamantyl, norbornyl, cyclohexyl, terpene and the like, or a bulky alkyl group such as isopropyl, sec-butyl, iso-amyl and the like.

In another aspect thereof, the present invention provides a process for the preparation of a resist material which comprises an alkali-insoluble, acid-sensitive polymer having a repeating unit containing a protected alkali-soluble group in which unit an alkali-soluble group is cleaved with an acid to thereby render said polymer alkali-soluble, said process comprising the steps of:

reacting an aldehyde or ketone compound and an acid halide compound, each of which has a structure necessary to complete a part of the repeating unit of said polymer, in a one pot reaction in the presence of at least one compound represented by the above-described formulae (I), (II) and (III);

polymerizing the resulting esters by themselves or with other monomeric compound in the presence of a polymerization initiator; and mixing the thus obtained acid-sensitive polymer with a photoacid generator capable of producing an acid upon exposure to a patterning radiation.

Using the preparation process of the present invention, it becomes possible to prepare the resist material in a simplified method and, with regard to the thus obtained resist material, it becomes possible to obtain a high resolution, a high sensitivity and an excellent resistance to etching because of the structure and function of the acid-sensitive polymer constituting the resist material.

In a still another aspect thereof, the present invention provides a process for the production of a semiconductor device, which comprises the steps of:

reacting an aldehyde or ketone compound and an acid halide compound in a one pot reaction in the presence of at least one compound represented by the above-described formulae (I), (II) and (III);

polymerizing the resulting esters by themselves or with other monomeric compound in the presence of a polymerization initiator;

mixing the resulting acid-sensitive polymer with a photoacid generator capable of producing an acid upon exposure to a patterning radiation to obtain a resist material;

coating the resist material on a surface of a semiconductor substrate; and subjecting a layer of said resist material to exposure, PEB (post exposure baking) and development steps to thereby form a resist pattern on said substrate.

DESCRIPTION OF THE PREFERRED EMBODIMENT

The preparation process of esters according to the present invention, as briefly described above, is characterized by reacting an aldehyde or ketone compound and an acid halide compound, each of which has a structure corresponding to a part of the target esters, in a so-called "one pot" reaction in the presence of at least one compound selected from the Gringnard compounds represented by the above formulae (I) and (II) as well as the organic lithium compounds represented by the above formula (III).

In principle, the aldehyde or ketone compound used as a starting material in the one pot esterification process of the present invention includes a variety of organic compounds which are well-known as aldehyde and ketone compounds in the field of organic chemistry, that is, those represented by the formula: RCHO in which R is hydrogen or alkyl, and characterized by unsaturated carbonyl group (C=O), and those having the carbonyl group (C=O) attached to two alkyl groups, respectively. Suitable aldehyde and ketone compounds particularly include the ketone compounds containing an alicyclic hydrocarbon group in a molecule thereof. More preferably, the alicyclic hydrocarbon group-containing aldehyde and ketone compounds include the compounds in which a carbon atom of the carbonyl group is one member of the ring structure of the alicyclic hydrocarbon group.

Accordingly, the esters obtained according to the preparation process of the present invention is preferably the ester compound which contains an alicyclic hydrocarbon group-containing moiety represented by the following formula (IV):

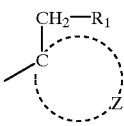
(IV)

in which $R_1$ represents a hydrogen atom or a substituted or unsubstituted alkyl group such as lower alkyl, for example, methyl, ethyl, propyl, isopropyl and the like, and Z represents atoms necessary to complete an alicyclic hydrocarbon group along with a carbon atom to which a —CH ,—R, group is bonded. The alicyclic hydrocarbon group which is completed by the Z atoms, although they are not restricted to, include those containing the following compounds as the skeleton:

(1) adamantane and derivatives thereof;
(2) norbornane and derivatives thereof;
(3) perhydroanthracene and derivatives thereof;
(4) perhydronaphthalene and derivatives thereof;
(5) tricyclo[5. 2. 1. $0^{2.6}$]decane and derivatives thereof;
(6) bicyclohexane and derivatives thereof;
(7) spiro [4, 4]nonane and derivatives thereof; and
(8) spiro[4, 5]decane and derivatives thereof.

These compounds have the following structures, respectively:

(1)

(2)

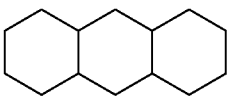
(3)

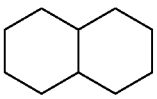
(4)

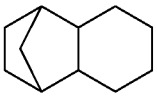
(5)

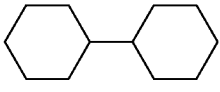
(6)

(7)

-continued

(8)

In the practice of the present invention, the alicyclic hydrocarbon groups which contain two or more ring structures or condensed rings, as above mentioned, can be advantageously used because, in the preparation of the resist polymer or copolymer from the alcohol esters as the starting material, an alicyclic group such as cyclohexyl and the like is insufficient to obtain a satisfactory resistance to dry etching. Further, among the above-described examples of suitable alicyclic hydrocarbon groups, if it is intended to obtain an excellent resistance to dry etching comparable to or higher than that of the conventional novolak resists, it is more preferred to use as the alicyclic hydrocarbon groups those containing condensed ring(s), such as adamantane. Accordingly, the most preferred ketone compound is 2-adamantanone.

Further, the ketone compound used in the practice of the present invention may contain bulky alkyl groups such as isopropyl, sec-butyl, iso-amyl and the like, in place of or in combination with the alicyclic hydrocarbon group described above.

The acid halide compound used in combination with the aldehyde or ketone compound in the practice of the present invention, as in the above-described aldehyde or ketone compound, include different halides of a variety of acids. Suitable acid halide compounds, although they are not restricted, include halides such as chlorides and the like of carboxylic acid such as acrylic acid, methacrylic acid, itaconic acid, fumaric acid and the like, sulfonic acid and other acids, or a α-substituted body thereof.

As above described, the presence of the Gringnard compound and/or the organic lithium compound is essentially required in the one pot esterification of the present invention.

The Gringnard compound which can be used in the practice of the present invention includes an organic magnesium compound widely known as the Gringnard reagent. Suitable Gringnard compounds are the magnesium compound represented by the following formula (I) or (II):

RMgX (I)

RMgX/CuX (II)

in which
R represents a hydrocarbon group, for example, an aliphatic group such as methyl, ethyl, propyl and the like, or an aromatic group such as phenyl and the like, and
X represents a halogen atom such as chlorine, iodine and the like. The Gringnard compounds which can be particularly advantageously used, although they are not restricted, include $CH_3MgBr$, $C_2H_5MgBr$, $C_4H_9MgBr$ and the like. These Gringnard compounds may be used alone or in combination.

Further, suitable organic lithium compounds are those represented by the following formula (III):

RLi or $R(CuLi)_{1/2}$ (III)

in which R is as defined above. The organic lithium compounds which can be particularly advantageously used, although they are not restricted, include $CH_3Li$, $C_4H_9Li$ and the like. These lithium compounds may be used alone or in combination.

Using the starting materials described in the above paragraphs, the one pot esterification process of the present invention for the preparation of the esters can be carried out under esterification conditions which are conventional for the well-known esterification processes. For example, it is preferred that each of the aldehyde or ketone compound, the acid halide compound, the Gringnard compound and the organic lithium compound is used in the range of from an equimolar amount to 2 equivalent amount.

The temperature and time for the esterification reaction may be widely varied, however, it is generally preferred that the esterification temperature is in the range of about −50° C. to room temperature, and the esterification time is about 24 hours. Note, however, that, of the described conditions, each is the condition which is generally considered to be preferred in the practice of the present invention, and accordingly they may be out of the range of the described conditions, if necessary, depending upon the desired results.

The preparation process for the resist material according to the present invention, as described hereinbefore, is directed to the production of a resist material containing an acid-sensitive polymer which is insoluble in an alkali, more particularly, an alkaline developing solution, and which has a repeating unit containing a protected alkali-soluble group which can be cleaved with an acid to thereby render the polymer alkali-soluble. The preparation process of the resist material is characterized by comprising the steps of:

reacting an aldehyde or ketone compound and an acid halide compound which are necessary to complete the repeating unit of the target acid-sensitive polymer and each of which has a structure corresponding to a part of the repeating units, in the presence of at least one compound represented by the above formulae (I), (II) and polymerizing the resulting esters by themselves or with one or more of other monomers in the presence of a polymerization initiator, and mixing the thus obtained acid-sensitive polymer with other components necessary to complete the target resist material including a photoacid generator (PAG) capable of producing an acid upon exposure to a patterning radiation.

In the practice of the present invention, the first step of the resist preparation, i.e., preparation of the esters, can be advantageously carried out in the manner described in detail hereinbefore.

After the ester, namely, the monomer used as the starting material in the production of the acid-sensitive polymer, has been prepared, the obtained monomer is solely polymerized to make an acid-sensitive homopolymer or copolymerized with one or more of other monomers to make an acid-sensitive copolymer. In principle, the polymerization or copolymerization process can be carried out in the presence of a suitable polymerization initiator, and other additives such as a catalyst and the like, and in accordance with conventional polymerization methods generally well-known in the field of polymer chemistry. For example, the copolymerization process includes alternating copolymerization, random copolymerization, block copolymerization, graft copolymerization and the like.

In the preparation of the acid-sensitive polymer in the form of a copolymer upon polymerization of the ester with other monomer(s), the other monomer []s used are not restricted to specific monomers. Preferably, the monomers used for the copolymerization, although they are not restricted, include (meth)acrylic acid ester and derivatives thereof, itaconic acid ester and derivatives thereof, fumaric acid ester and derivatives thereof, styrene substituent and derivatives thereof, and others. These monomers are considered to be more desirable than other possible monomers, in view of the preparation of the copolymer and the coatability of the copolymer. Further, if desired, the acid-sensitive copolymer may be prepared by using, in combination, the above-mentioned repeating units and other repeating units which include, although they are not restricted to, acrylonitriles, olefine, dienes or derivatives thereof.

In the acid-sensitive polymer or copolymer used in the present invention, in order to attain a satisfactory adhesion of the resist material to the underlying substrate or layer, it is more preferred that the polymer or copolymer contains a repeating unit having a strong polarity. Particularly, if they contain a repeating unit which is by itself soluble in an alkali solution, in addition to the essential component, i.e., alkali-soluble group, such a combination of the repeating units in the polymer or copolymer enables the resulting resist material to be developed with an alkaline solution, as a function of a small amount of carboxylic acid originated from the protected alkali-soluble group, and others.

For the preparation process of the present invention, it is desirable that a specific resist material can be obtained in which material the acid-sensitive polymer as one component of the resist material is in the form of a copolymer and, in addition to the repeating unit originated from the above-described ester, the repeating units of the copolymer include the repeating unit containing an alkali-soluble group in a side chain thereof and/or the repeating unit containing additional, protected alkali-soluble group, capable of being cleaved with an acid produced from the photoacid generator (PAG), in a side chain thereof.

Preferably, the acid-sensitive copolymer as said desirable resist material may have the structural unit represented by the following formula (V) or (VI):

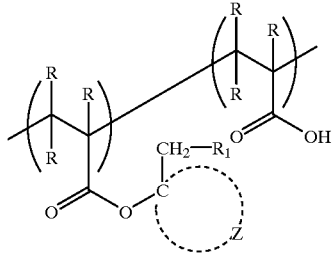

(V)

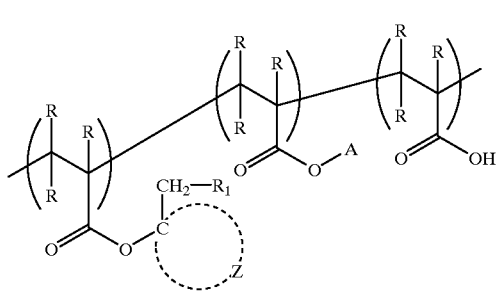

(VI)

in which
R may be the same or different, and each represents a hydrogen, a halogen or a substituted or unsubstituted, straight chain or branched chain alkyl group of 1 to 4 carbon atoms, A represents a protective moiety capable of being cleaved with an acid, and $R_1$ and Z each is as defined above.

The structural unit represented by the above formula (V) is illustrative of introducing, into the structure of the copolymer, in combination, a protective group containing an alicyclic skeleton such as adamantane or norbornane and capable of being cleaved with an acid generated from a photoacid generator, and an alkali-soluble carboxylic acid group. After exposure of the resist film, an exposed area of the resist film can be easily dissolved in an alkaline developing solution, since said resist copolymer contains an acidic group, i.e., a carboxylic group, in the structure thereof. Further, the control of the content of the acidic group in the resist copolymer makes the exposed resist film developable with . a currently standard alkaline developer such as an aqueous solution of 2.38% tetramethylammonium hydroxide (TMAH). In this instance, the content of the carboxylic acid-containing unit in the resist copolymer is preferably less than 2% by mole or not less than 5% by mole.

Further, the structural unit represented by the above formula (VI) is illustrative of introducing, in the structure of the copolymer, in combination, a protective group, containing an alicyclic skeleton such as adamantane or norborane and capable of being cleaved with an acid generated from a photoacid generator, a conventional protective group which is distinguished from said alicyclic skeleton-containing protective and which is able to be cleaved with the acid generated from the photoacid generator, and an alkali-soluble carboxylic acid group. If the resist material containing the described copolymer is intended to be used in excimer lithography using ArF excimer laser light having a wavelength of 193 nm as an exposure source, it is preferred to exclude aromatic ring(s) from the protective group. Using the described structural unit, it becomes possible to attain a smooth development of the exposed resist film with an alkaline developer, even if the intended cleavage of the protective group could not be induced due to any problem.

In the above structural units of the formulae (V) and (VI), the substituent R may be methyl, ethyl, and those substituted with halogen such as chlorine or bromine. The substituent A capable of being cleaved with an acid may be a conventional protective group such as a tertiary carbon group such as t-butyl or t-amyl, or β-oxyketone group such as 3-oxycyclohexyl, mevalonic lactone, and the like. Moreover, the alicyclic hydrocarbon group completed by the atoms Z may be adamantyl and derivatives thereof, norborane and derivatives thereof, perhydroanthacene and derivatives thereof, perhydronaphthalene and derivatives thereof, tricyclo[5. 2. 1. $0^{2.6}$]decane and derivatives thereof, spiro[4, 4]nonane and derivatives thereof as well as spiro [4, 5]decane and derivatives thereof, mentioned above with the structures thereof.

The acid-sensitive polymer or copolymer which is preferably prepared by using the method of the present invention will be further described particularly with reference to those containing a carboxylic group as the alkali-soluble group.

Preferably, the acid-sensitive polymer is (meth)acrylate polymer represented by the following formula (VII):

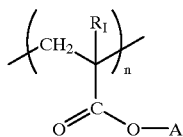

(VII)

in which

R_I represents a proton (hydrogen), halogen or substituted or unsubstituted alkyl group such as methyl, ethyl or methylol, A corresponds to the above-mentioned moiety (I), and represents a protective group, preferably a protected group of alicyclic hydrocarbon group containing an ester bond as a part of the ring structure and being substituted with an alkyl group, more preferably, adamantyl, norbornyl, cyclohexyl, tricyclo[5. 2. 1. 0]decane and other alicyclic groups, and n is any positive integer.

The acid-sensitive copolymer is preferably (meth)acrylate copolymer represented by the following formula (VIII) or (IX). Although not shown, the (meth)acrylate terpolymer can be represented by a similar structure except for the third repeating unit added.

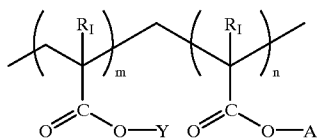

(VIII)

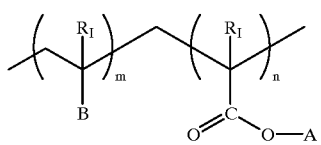

(IX)

in which

R_I, A and n each is as defined above,

Y represents any substituent such as, preferably, an alkyl group, for example, t-butyl and the like, an ether group, for example, phenoxy and the like, an alicyclic hydrocarbon group, for example, adamantyl, norbornyl, cyclohexyl, tricyclo[5. 2. 1. 0]decane and the like, or the groups represented by the following formulae:

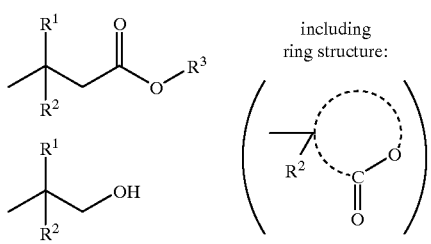

including ring structure:

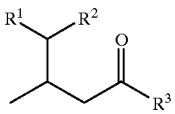 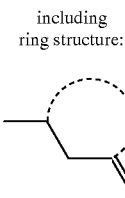

in which $R^1$, $R^2$ and $R^3$ each represents hydrogen, substituted or unsubstituted alkyl or alkylene group such as methyl, ethyl or methylene, and others, B represents any substituent, for example, preferably, a carboxyl group or the group represented by the following formula:

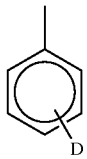

in which D represents —$OR^4$/—$COOR^4$ or —OCO—$R^4$ wherein $R^4$ in the substituent D each represents hydrogen or a substituted or unsubstituted alkyl group such as methyl or ethyl, and m and n each is any positive integer.

In addition, if desired, the above-described acid-sensitive polymer or copolymer may contain an alkali-soluble polymer or copolymer such as novolak resin, phenol resin, imide resin, carboxylic acid-containing resin and the like.

In the preparation process of the present invention, the polymerization of the ester can be carried out by polymerizing the ester and, if desired, other selected monomer(s) in the presence of a suitable polymerization initiator, as is explained hereinbefore. The conditions for the polymerization and the initiators used may be freely selected from the wide variety of well-known conditions and initiators. Typical examples of suitable polymerization initiators include, for example, the following compounds.

AIBN (azoisobutylonitrile):

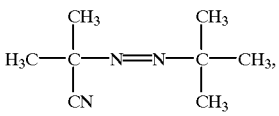

MAIB (dimethyl-2,2-azoisobisbutylate):

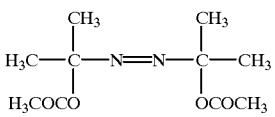

After the preparation of the acid-sensitive polymer or copolymer, the resulting polymer or copolymer is dissolved in a suitable solvent, preferably an organic solvent, along with a photoacid generator (PAG) to form a resist solution. The photoacid generator used in combination with the acid-sensitive polymer or copolymer may be any conventional agent which is well-known as a photoacid generator (PAG) in resist chemistry, namely, compounds capable of generating a protonic acid upon exposure of the resist material to a patterning radiation such as ultraviolet radiation, far ultraviolet radiation, vacuum ultraviolet radiation, electron beam, X-ray and laser light. Typical examples of the photoacid generator suitably used in the practice of the present invention include various compounds described hereinafter, although the present invention should not be restricted to these compounds.

(1) diazonium salts represented by the following formula:

in which

Ar represents a substituted or unsubstituted aromatic group, for example, phenyl group or phenyl group substituted with halogen such as chlorine, bromine, iodine or fluorine, alkyl such as methyl or t-butyl, aryl or other substituent groups, or a substituted or unsubstituted alicyclic hydrocarbon group, and X represents halogen, $BF_4$, $BF_6$, $PF_6$, $AsF_6$, $SbF_6$, $CF_3SO_3$, $ClO_4$ or anion of organic sulfonic acids.

(2) iodonium salts represented by the following formula:

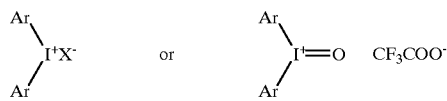

in which Ar and X are as defined above.

(3) sulfonium salts represented by the following formulae:

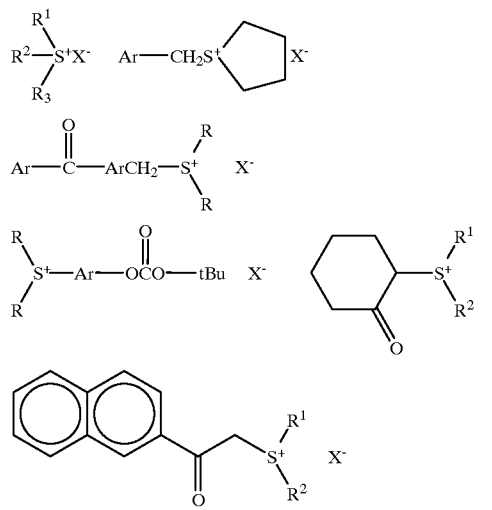

in which R, $R^1$, $R^2$, $R^3$, Ar and X each is as defined above, and, for example, R is methyl and $R^1$, $R^2$ and R3 each is phenyl, and tBu is t-butyl.

(4) sulfonic esters represented by the following formula:

or

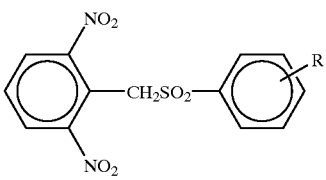

in which Ar and R are as defined above.

(5) oxazole derivatives represented by the following formula:

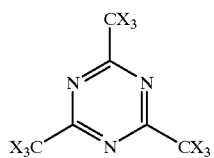

in which X is as defined above with the proviso that at least one of the substituents —$CX_3$ is a substituted or unsubstituted aryl or alkenyl.

(6) s-triazine derivatives represented by the following formula:

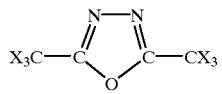

in which X is as defined above with the proviso that at least one of the substituents —$CX_3$ is a substituted or unsubstituted aryl or alkenyl.

(7) disulfone derivatives represented by the following formula:

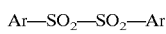

in which
Ar is as defined above.

(8) imide compounds represented by the following formula:

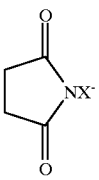 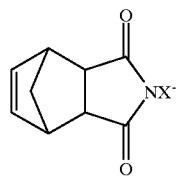

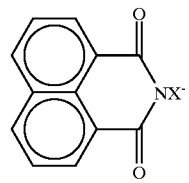 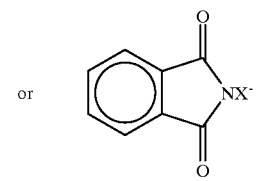

in which X is as defined above.

(9) others such as oxime sulfonate, diazonaphtoquinone, benzoine tosylate and the like.

The content of the PAG compounds in the resist material may be widely varied depending upon factors such as the acid releasing capability of the PAG compound used, the level of the patterning radiation and the like. The content of the PAG compounds in the resist material is generally in the range of about 1 to 3% by weight, based on the total weight of the resist material, preferably in the range of about 1 to 15% by weight.

The organic solvent used in the preparation of the resist solution may vary widely depending on various factors such as the resist material used, coating conditions and the like, and typical examples of suitable organic solvents, although they are not restricted to the below-mentioned, include cyclohexanone, propyleneglycol methyletheracetate (PGMEA), ethyl lactane, methyl amyl ketone, methyl-3-methoxypropionate, ethyl-3-ethoxypropionate, diacetoalcohol, ethyl pyruvicate and similar solvents. These organic solvents may be used alone or, if desired, may be used as a mixture of two or more solvents. The amount of the organic solvent used is not restricted, however, it is preferred that the solvent be used in an amount sufficient to provide a resist coating having a desired layer thickness and a viscosity suitable for coating such as spin coating.

In the preparation of the resist solution, if desired, an auxiliary solvent may be used in addition to the above-described organic solvent (hereinafter referred to as "main solvent"). The auxiliary solvent is not required if the resist components can be easily dissolved in the main solvent, however, if the resist components can hardly be dissolved in the main solvent, the auxiliary solvent will assist in dissolving the resist components in the main solvent. Useful auxiliary solvents, although they are not restricted to those below-mentioned, include butyl acetate, γ-butylolactone, propyleneglycol methylether and similar solvents.

Using the resist material obtained according to the preparation process of the present invention, resist patterns can be formed on a substrate in accordance with conventional lithographic processes. A series of process steps which can be advantageously adopted in the practice of the present invention will be described hereinafter. Note, however, that the present invention should not be restricted to the described steps, and accordingly any modifications or variations can be applied to the described process of the present invention within the spirit and scope of the present invention.

First, a solution of the chemically amplified resist is coated on a substrate to be fabricated, to thereby form a resist layer having a predetermined thickness. The substrate used herein may be any conventional substrate used in the field of semiconductor devices and other devices, and typical examples of suitable substrates include a silicon substrate, a glass substrate, a SOS substrate, a non-magnetic substrate such as ceramic substrate and the like. If desired, the substrate may additionally contain one or more overlaying layers such as a polysilicon layer, an oxide layer, for example, a silicon oxide layer, a nitride layer, for example, a silicon nitride layer, a metallic layer, for example, an aluminum layer, an insulating interlayer, a magnetic layer and the like. Further, the substrate and/or the overlaying layer(s) may contain any elements such as wiring or circuits fabricated therein. Furthermore, in order to increase the adhesion strength of the resist layer to the substrate, a surface of the substrate may be subjected to a conventional hydrophobic treatment. Typical examples of the chemicals advantageously used in this treatment are 1,1,1,3,3,3-hexamethyldisilazane (HMDS) and the like.

Coating of the resist solution can be preferably carried out by spin-coating although any other conventional coating method such as roller coating and dip coating may be used, if desired. The thickness of the resist layer is generally in the range of about 0.1 to 200 $\mu$m, and preferably in the range of about 0.3 to 2.0 $\mu$m. Note, however, that the thickness of the resist layer may be varied depending upon different factors such as the intended use of the resulting resist patterns.

The resist layer on the substrate is generally, and preferably, prebaked at a temperature of about 60 to 150° C., more preferably about 60 to 100° C., for about 60 to 180 seconds, before selective exposure of the layer to a patterning radiation. Prebaking may be carried out by using any heating means conventionally used in the resist process. Suitable heating means include, for example, a hot plate, infrared (IR) heating oven, microwave heating oven and the like.

In addition, if a topcoat layer or protective layer is to be applied over the resist layer, it is possible to spin-coat a solution of olefinic resin over the resist layer, followed by baking the olefinic coating at a temperature of about 100° C.

Next, the optionally prebaked resist layer is selectively exposed to a patterning radiation in conventional exposure devices or aligners. Suitable exposure devices include commercially available devices such as ultraviolet (far UV, deep UV or vacuum UV) exposure devices, X-ray exposure devices, electron beam exposure systems and excimer steppers, for example. The conditions of exposure can be varied to select the optimum condition in each process, taking various factors into consideration. As a result of the selective exposure, the photoacid generator (PAG) in the exposed areas of the resist layer is decomposed, and thus the exposed resist layer is now ready for dissolving off from the substrate in the subsequent development step using an alkaline developer.

After completion of the selective exposure, the exposed resist layer is heated on a heating means such as a hot plate. The heating is called "Post-Exposure Baking" (PEB), and PEB is preferably carried out at a temperature sufficient to cause cleavage of the protective group from the protected alkali-soluble group in the acid-sensitive polymer in the resist layer in the presence of a catalytic acid produced from the photoacid generator. PEB may be carried out in a manner similar to that of the above-described prebaking, and generally it can be carried out at a temperature of about 60 to 150° C., preferably about 100 to 150° C., for about 30 to 240 seconds. Further, when the resist layer is used in combination with the topcoat layer, it is possible to separate and remove the topcoat layer in any suitable manner such as use of an organic solvent, after PEB and before the development.

As a final step of the present process, the heated resist layer is developed with an alkaline solution such as an aqueous alkaline solution or an alcoholic alkaline solution as a developer in accordance with any conventional method. Suitable apparatuses for use in this development step include the well-known developers such as a spin developer, dip developer and spray developer.

Typical examples of the alkaline solution suitable as the developer include an aqueous or alcoholic solution of hydroxides of metals belonging to the groups I and II of the periodic table such as potassium hydroxide or an aqueous or alcoholic solution of organic bases free from metal ions such as tetraalkylammonium hydroxide, typical examples of which will be described hereinafter with reference to the chemical formulas thereof. Further, if desired, the alkaline solution used as the developer may additionally contain any additive, such as a surface active agent, in order to improve the resulting development effect. Furthermore, if it is appropriate, as the inventors have suggested in Japanese Unexamined Patent Publication (Kokai) No. 7-23053, the developer used herein may be an aqueous or alcoholic solution containing as the developer an ammonium compound represented by the following formula:

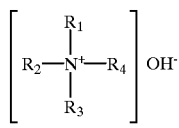

in which $R_1$, $R_2$, $R_3$ and $R_4$ may be the same or different, and each represents a substituted or unsubstituted alkyl group of 1 to 6 carbon atoms, a morpholine compound represented by the following formula:

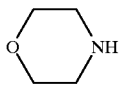

or a mixture thereof. The ammonium compound useful as the developer, although it is not restricted to the below-mentioned, includes:

tetramethylammonium hydroxide (TMAH),
tetraethylammonium hydroxide (TEAH),
tetrapropylammonium hydroxide (TPAH),
tetrabutylammonium hydroxide (TBAH), and the like. More preferably, tetramethylammonium hydroxide (TMAH) can be used as the developer.

The developer is dissolved in water or an alcohol such as methanol, ethanol, isopropyl alcohol and the like to obtain a developing solution. The concentration of the developer in the developing solution may be widely varied, however, it is generally in the range of about 0.1 to 15% by weight, preferably in the range of about 0.1 to 10% by weight. The developing time may also be widely varied, however, it is generally in the range of about 1 to 5 minutes, preferably in the range of about 1 to 3 minutes. As a result of development, the exposed areas of the resist layer are dissolved and removed from a surface of the substrate, thereby forming the desired positive resist patterns corresponding to the exposure pattern. Finally, the resulting resist patterns are rinsed with deionized water, and dried in accordance with the conventional manner.

The thus obtained resist patterns can be advantageously utilized in the production of semiconductor devices according to the present invention.

As can be understood from the above-mentioned descriptions and the appended working examples, according to the present invention, since the ketone compound and the acid halide compound are reacted in the presence of the above-described compound is) of the formula (I), (II) and/or (III), it becomes possible to easily and stably produce esters having a large steric hindrance with a high yield. Further, since the obtained esters can be used as a monomer in the preparation of the acid-sensitive polymer and the resulting polymer can be used as a base resin, it becomes possible to easily produce high performance resist material in the simplified production steps. Actually, if the formation of resist patterns is carried out by using the resist material obtained in accordance with the preparation process of the present invention, it becomes possible to form fine resist patterns particularly suitable for the production of semiconductor devices, that is, resist patterns having a high sensitivity, high resolution and excellent resistance to dry etching.

EXAMPLES

The present invention will be further described with reference to the appended working examples. Note, however, that the examples are included herein only for explanation purposes and they are not intended to restrict the present invention.

Example 1

Preparation of 2-methyl-2-adamantyl methacrylate from 2-adamantanone in the presence of methyl lithium 5.0 g (0.033 mole) of 2-adamantanone and 50 ml of tetrahydrofuran (THF) were charged in a three neck flask, and were stirred under an argon atmosphere, until the 2-adamantanone was completely dissolved in THF. After completion of stirring, the contents of the flask were cooled with dry ice/acetone to a temperature of not more than −40° C. Then, while the content of the flask was maintained at a temperature of −20 to −40° C., a hexanone solution of methyl lithium in an amount of 28.3 ml (1.2 equivalents based on 2-adamantanone) was slowly dropwise added to the mixture. After completion of dropwise addition, stirring was further continued for 30 minutes, and then 4.2 ml (1.3 equivalents based on 2-adamantanone) of methacrylic chloride was slowly dropwise added to the mixture. The reaction was further continued at −20° C. for 2 hours, and then at a room temperature for one hour. After completion of the reaction, a small amount of crushed ice was added to the resulting mixture under water cooling conditions to thereby inactivate an excess amount of methyl lithium. Thereafter, 50 ml of a mixture of saturated brine and hexane was added to the mixture, followed by intimate stirring. An organic layer was separated from the mixture, washed with a saturated aqueous solution of sodium hydrogencarbonate and then with a saturated brine, and dried on anhydrous magnesium sulfate. The resulting product was concentrated to obtain 8.4 g of a raw product (yield: 107.7%). Following concentration, the raw product was purified on a column of silica gel to obtain 7.3 g of a pure product (yield: 95.0%). An analysis of the thus obtained product indicated that the product was the target compound, i.e., 2-methyl-2-adamantyl methacrylate.

Example 2

Preparation of 2-methyl-2-adamantyl methacrylate from 2-adamantanone in the presence of methyl magnesium bromide 5.0 g (0.033 mole) of 2-adamantanone and 50 ml of tetrahydrofuran (THF) were charged in a three neck flask, and were stirred under an argon atmosphere, until the 2-adamantanone was completely dissolved in THF. After completion of stirring, a hexanone solution of methyl magnesium bromide in an amount of 42.9 ml (1.2 equivalents based on 2-adamantanone) was dropwise added to the mixture. After completion of dropwise addition , the mixture was left to stand for one hour, and 4.2 ml (1.2 equivalents based on 2-adamantanone) of methacryloylchloride was slowly dropwise added to the mixture. The reaction was further continued at −20° C. for 2 hours, and then at room temperature for one hour. After completion of the reaction, a small amount of crushed ice was added to the resulting mixture under water cooling conditions to thereby inactivate an excess amount of methyl magnesium bromide. Thereafter, 50 ml of a mixture of saturated brine and hexane was added to the mixture, followed by intimate stirring. An organic layer was separated from the mixture, washed with a saturated aqueous solution of sodium hydrogencarbonate and then with a saturated brine, and dried on anhydrous magnesium sulfate. The resulting product was concentrated to obtain 8.4 g of a raw product. Following concentration, the raw product was purified on a column of silica gel to obtain 6.5 g of a pure product (yield: 85.0%). An analysis of the thus obtained product indicated that the product was the target compound, i.e., 2-methyl-2-adamantyl methacrylate.

Comparative Example 1

Preparation of 2-methyl-2-adamantyl methacrylate from 2-methyl-2-adamantanol in the presence of triethyl amine 150 g (0.9 mole) of 2-methyl-2-adamantanol, 900 ml of tetrahydrofuran (THF) and 132 ml of methacrylic chloride were charged in a three neck flask, and stirred. The contents of the flask were cooled on an ice bath, and maintained at a temperature of not more than 10° C. 226 g of triethyl amine was slowly dropwise added to the resulting reaction mixture. After the mixture was reacted overnight at an ordinary temperature, iced water was portionwise added to the mixture. The reaction was further continued at −20° C. for 2 hours, and then at room temperature for one hour. An organic layer was separated from the mixture, washed with a saturated aqueous solution of sodium hydrogencarbonate and then with a saturated brine, and dried on anhydrous magnesium sulfate. The resulting product was concentrated to obtain 180 g of a raw product. Following concentration, the raw product was purified on a column of silica gel to obtain 161.4 g of a pure product (yield: 76.5%). An analysis of the thus obtained product indicated that the product was the target compound, i.e., 2-methyl-2-adamantyl methacrylate.

Comparative Example 2

Preparation of 2-methyl-2-adamantyl methacrylate from 2-methyl-2-adamantanol in the presence of pyridine The procedure of Comparative Example 1 was repeated with the proviso that under the cooling conditions, 24 ml of pyridine was slowly dropwise added to a mixture of 22.6 g (0.136 mole) of 2-methyl-2-adamantanol, 130 ml of THF and 26.6 g of methacrylic chloride. The raw product was purified on a column of silica gel to obtain 12.1 g of the target product, i.e., 2-methyl-2-adamantyl methacrylate, (yield: 39.0%). It was confirmed that the product contained a remarkable amount of impurities.

Example 3

Preparation of 2-butyl-2-adamantyl methacrylate from 2-adamantanone in the presence of butyl lithium 27.2 g (0.181 mole) of 2-adamantanone and 300 ml of tetrahydrofuran (THF) were charged in a three neck flask, and were stirred under an argon atmosphere, until 2-adamantanone was completely dissolved in THF. After completion of stirring, a content of the flask was cooled with dry ice/acetone to a temperature of not more than −40° C. Then, while the content of the flask was maintained at a temperature of −20 to −40° C., a hexanone solution of butyl lithium in an amount of 136 ml (1.2 equivalents based on 2-adamantanone) was slowly dropwise added to the mixture (over about 50 minutes). Without changing the reaction conditions, the reaction was further continued for one hour, and then 22 ml (1.3 equivalents based on 2-adamantanone) of methacrylic chloride was slowly dropwise added to the mixture (over about 36 minutes). After completion of the dropwise addition, the reaction was further continued at −40° C. for about one hour. After completion of the reaction, a small amount of crushed ice was added to the resulting mixture, under water cooling conditions, to thereby inactivate an excess amount of butyl lithium. Thereafter, 50 ml of a mixture of saturated brine and hexane was added to the mixture, followed by intimate stirring. An organic layer was separated from the mixture, washed with a saturated aqueous solution of sodium hydrogencarbonate and then with a saturated brine, and dried on anhydrous magnesium sulfate. The resulting product was concentrated to obtain 56.8 g of a raw product (yield: 107.4%). Following concentration, the raw product was purified on a column of silica gel to obtain 50.2 g of a pure product (yield: 95.0%). An analysis of the thus obtained product indicated that the product was the target compound, i.e., 2-butyl-2-adamantyl methacrylate.

Comparative Example 3

Preparation of 2-butyl-2-adamantyl methacrylate from 2-butyl-2-adamantanol in the presence of triethyl amine 5 g (0.02 mole) of 2-butyl-2-adamantanol, 500 ml of tetrahydrofuran (THF) and 47 ml (2 equivalents based on 2-butyl-2-adamantanol) of methacrylic chloride were charged in a three neck flask, and stirred. A content of the flask was cooled on an ice bath, and maintained at a temperature of not more than 10° C. 7.7 ml (2.3 equivalents based on 2-butyl-2-adamantanol) of triethyl amine was slowly dropwise added to the resulting reaction mixture. After the mixture was reacted overnight at an ordinary temperature, the reaction product was treated, concentrated and dried in accordance with the conventional method. As a result, 2-butyl-2-adamantanol used as the starting material was recovered. No target product, i.e., 2-butyl-2-adamantyl methacrylate, was recovered.

Comparative Example 4

Preparation of 2-butyl-2-adamantyl methacrylate from 2-butyl-2-adamantanol in the presence of metallic magnesium 1 g (0.05 mole) of 2-butyl-2-adamantanol, 10 ml of tetrahydrofuran (THF) and 0.9 mole (2 equivalents based on 2-butyl-2-adamantanol) of methacrylic chloride were charged in a three neck flask, and stirred. Next, 0.35 g (3 equivalents based on 2-butyl-2-adamantanol) of metallic magnesium was added to the resulting reaction mixture. After the mixture was reacted overnight at an ordinary temperature, the reaction product was treated, concentrated and dried in accordance with the conventional method. As a result, 2-butyl-2-adamantanol used as the starting material was recovered. No target product, i.e., 2-butyl-2-adamantyl methacrylate, was recovered.

Comparative Example 5

Preparation of 2-butyl-2-adamantyl methacrylate from 2-butyl-2-adamantanol in the presence of hydrogenated sodium Under an argon atmosphere, 1.7 g (0.007 mole) of 2-butyl-2-adamantanol was added to a mixture of 0.2 g (1.1 equivalent) of hydrogenated sodium and 10 ml of tetrahydrofuran (THF). The resulting mixture was heated and refluxed for 3 hours with stirring. After cooling to about 10° C., 0.9 g (2 equivalents based on 2-butyl-2-adamantanol) of methacrylic chloride was gradually added to the resulting reaction mixture. After the mixture was reacted overnight at an ordinary temperature without changing the reaction conditions, the reaction product was treated, concentrated and dried in accordance with the conventional method. As a result, 2-butyl-2-adamantanol used as the starting material was recovered. No target product, i.e., 2-butyl-2-adamantyl methacrylate, was recovered.

Example 4

Preparation of a copolymer of 2-butyl-2-adamantyl methacrylate and mevalonic lactone methacrylate 2-butyl-2-adamantyl methacrylate and mevalonic lactone methacrylate in a ratio of 1:1 as starting monomers were charged into a polymerization container to make a 1,4-dioxane solution containing 3 mole/L of the monomers. After addition of 15 mole% of 2,2'-azobisisobutylonitrile (AIBN), as a polymerization initiator, to the 1,4-dioxane solution, the monomers were polymerized at 80° C. for about 9 hours. After completion of the polymerization, the polymerization product was purified by using methanol as a precipitant. The copolymer of 2-butyl-2-adamantyl methacrylate and mevalonic lactone methacrylate represented by the following formula was obtained.

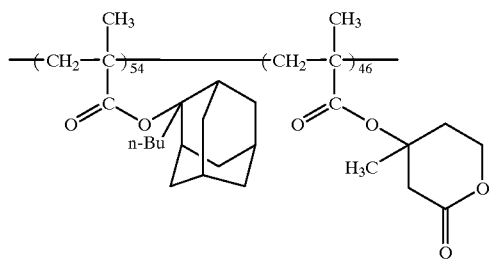

The resulting copolymer had a composition ratio (m:n) of 54:46, weight average molecular weight (Mw) of 7,540 (polystyrene standard-equivalent) and degree of polydispersion (Mw/Mn) of 1.8.

Example 5

Formation of Resist Patterns

Triphenylsulfonium triflate (TPSSO$_3$CF$_3$) as a photoacid generator (PAG) in an amount of 2 wt. % with regard to the copolymer was added to the copolymer of 2-butyl-2-adamantyl methacrylate and mevalonic lactone methacrylate prepared in Example 4, and the mixture was dissolved in cyclohexanone to make a resist solution containing the copolymer in an amount of 14 wt. %. The resist solution was spin-coated on a silicon substrate which has been treated with HMDS, and prebaked at 100° C. for 60 seconds on a hot plate to form a 0.4-μm thick resist layer.

After prebaking, the resist layer was selectively exposed to a pattern of laser light having a wavelength of 193 nm in an ArF excimer laser exposure system (Nikon, NA=0.55). The exposed resist layer was then subjected to the post-exposure baking (PEB) on a hot plate at 100° C. for 60 seconds. The postbaked resist coating was developed with an aqueous solution of 2.38% (0.27N) tetramethylammonium hydroxide (TMAH), NMD-3 (trade name) commercially available from Tokyo Ohka Co., for 60 seconds, and rinsed for 30 seconds in a purified water. Positive resist patterns which corresponded to the pattern of the laser light as an exposure source were thus obtained. In this example, a threshold energy Eth of the exposure dose was 3 mJ/cm$^2$, and the resolution of the patterns was 0.17 μm L/S (line & space).

What is claimed is:

1. A process, for the preparation of esters of tertiary alcohol, which comprises reacting an aldehyde or ketone compound and an acid halide compound in a one pot reaction in the presence of at least one compound represented by the following formulae:

in which
R represents a hydrocarbon group, and
X represents a halogen atom, to directly form the esters without forming an intermediate alcohol.

2. The preparation process according to claim 1, in which said aldehyde or ketone compound contains an alicyclic hydrocarbon group in a molecule thereof.

3. The preparation process according to claim 2, in which a carbon atom of the carbonyl group in said aldehyde or ketone compound is one member of the ring structure of said alicyclic hydrocarbon group.

4. The preparation process according to claim 1, in which said esters contain an alicyclic hydrocarbon group-containing moiety represented by the following formula (IV):

in which
R$_1$ represents a hydrogen atom or an alkyl group, and
Z represents atoms necessary to complete an alicyclic hydrocarbon group along with a carbon atom to which a —CH$_2$—R$_1$ group is bonded.

5. The preparation process according to claim 4, in which said alicyclic hydrocarbon group is one member selected from the group consisting of:
(1) adamantane and derivatives thereof;
(2) norbornane and derivatives thereof;
(3) perhydroanthracene and derivatives thereof;
(4) perhydronaphthalene and derivatives thereof;
(5) tricyclo[5. 2. 1. 0$^{2,6}$]decane and derivatives thereof;
(6) bicyclohexane and derivatives thereof;
(7) spiro[4, 4]nonane and derivatives thereof; and
(8) spiro[4, 5]decane and derivatives thereof.

6. The preparation process according to any one of claims 1 to 5, in which said ketone compound is 2-adamantanone.

7. The preparation process according to any one of claims 1 to 5, in which said acid halide compound is a halide of carboxylic acid.

8. The preparation process according to claim 7, in which said halide of carboxylic acid is a halide of acrylic acid or a α-substituted body thereof.

9. The preparation process according to claim 1, wherein the esters are esters of a tertiary alcohol.

10. A process, comprising:

forming a mixture by adding an aldehyde or ketone compound, an acid halide compound and a compound represented by the following formulae $$RMgX \qquad (I)$$

$$RMgX/CuX \qquad (II); \text{ and}$$

$$RLi \text{ or } R(CuLi)_{1/2} \qquad (III);$$

in which

R represents a hydrocarbon group, and

X represents a halogen atom, to a reaction vessel, and allowing the mixture to react and form esters of tertiary alcohol directly without forming an intermediate alcohol.

* * * * *